US009066772B2

(12) United States Patent
Tchouprakov et al.

(10) Patent No.: US 9,066,772 B2
(45) Date of Patent: Jun. 30, 2015

(54) INTRA-ORAL SCANNING DEVICE WITH ILLUMINATION FRAMES INTERSPERSED WITH IMAGE FRAMES

(71) Applicant: D4D Technologies, LLC, Richardson, TX (US)

(72) Inventors: Andrei Tchouprakov, Plano, TX (US); Radu Gheorghe, Richardson, TX (US); Roman Sokolov, Richardson, TX (US); Mark Quadling, Plano, TX (US); Henley Quadling, Dallas, TX (US); Rod Duncan, Dallas, TX (US); Ye Li, Plano, TX (US)

(73) Assignee: D4D Technologies, LLC, Richardson, TX (US)

( * ) Notice: Subject to any disclaimer, the term of this patent is extended or adjusted under 35 U.S.C. 154(b) by 0 days.

(21) Appl. No.: 14/172,544

(22) Filed: Feb. 4, 2014

(65) Prior Publication Data

US 2014/0248576 A1 Sep. 4, 2014

Related U.S. Application Data

(60) Provisional application No. 61/760,533, filed on Feb. 4, 2013.

(51) Int. Cl.
| | |
|---|---|
| *G01C 11/12* | (2006.01) |
| *A61C 9/00* | (2006.01) |
| *A61B 1/253* | (2006.01) |
| *A61C 1/00* | (2006.01) |
| *A61C 1/08* | (2006.01) |
| *A61B 5/00* | (2006.01) |

(52) U.S. Cl.
CPC .................. *A61C 9/006* (2013.01); *A61B 1/253* (2013.01); *A61C 1/0046* (2013.01); *A61C 1/088* (2013.01); *A61C 9/0073* (2013.01); *A61B 5/0066* (2013.01)

(58) Field of Classification Search
CPC .................... G02B 2027/0178; G02B 27/017; G02B 2027/014; G02B 27/0093; G02B 2027/0187; G02B 2027/0118; G02B 27/0172; G02B 5/30; G02B 2027/0138; G02B 27/0176; G02B 2027/0127; G02B 2027/0132; G02B 27/0149
See application file for complete search history.

(56) References Cited

U.S. PATENT DOCUMENTS

| | | | |
|---|---|---|---|
| 5,372,502 A | 12/1994 | Massen et al. | |
| 7,184,150 B2 | 2/2007 | Quadling et al. | |
| 2003/0096210 A1 | 5/2003 | Rubbert et al. | |
| 2005/0099638 A1 | 5/2005 | Quadling et al. | |
| 2009/0061381 A1 * | 3/2009 | Durbin et al. | 433/24 |
| 2010/0284589 A1 | 11/2010 | Thiel et al. | |

OTHER PUBLICATIONS

International Search Report, PCT/US2014/014691, Apr. 28, 2014.

* cited by examiner

*Primary Examiner* — Michael P Stafira
(74) *Attorney, Agent, or Firm* — David H. Judson

(57) ABSTRACT

An intra-oral scanning device includes a light source and an optical system, and communicates with a display system. The device captures images of an object of interest, e.g., patient teeth or associated anatomy, by projecting the light source as a first series of frames, and a second series of frames. The first series of frames projects first pattern data, and the second series of frames projects second data. The second series of frames are interleaved between frames in the first series of frames. The frames in the first series are partially-illuminated and are used to capture data for a 3D model. The frames in the second series are preferably fully-illuminated and are used to generate a live preview of the object. By displaying the live preview frames in juxtaposition to the 3D model, the operator is provided with visual feedback of the object.

14 Claims, 5 Drawing Sheets

INTRA-ORAL SCANNING DEVICE WITH ILLUMINATION FRAMES INTERSPERSED WITH IMAGE FRAMES

BACKGROUND OF THE INVENTION

1. Technical Field

This disclosure relates generally to computer-assisted techniques for creating dental restorations.

2. Brief Description of the Related Art

During the last decade various technological advancements have increasingly started to be applied to systems in the healthcare arena, particularly in dental care. More specifically for example, traditional imaging and computer vision algorithms coupled with soft X-ray sensitive charge coupled device (CCD) based vision hardware have rendered conventional X ray photography ubiquitous, while more advanced data imaging and processing has enabled passive intraoral 3D topography. The latter comprises the acquisition portion of a CAD/CAM system, which would typically be followed by a design step using some sort of manipulating software, and a manufacturing step that might entail an office laser printer-sized milling machine. The entire system allows a dentist to provide a patient the same services a manufacturing laboratory would provide with a certain turnaround time, however, all chair-side and on-the-spot, greatly reducing the possibility of infections and discomfort to the patient. In addition, clinical cases containing raw and processed data are easily shared as digital files between dentists who lack the second portion of the system, i.e. the manufacturing step, and laboratories who have adapted and evolved to embrace CAD/CAM.

In a clinical case where a patient is required a crown, for example, traditionally the dentist would prepare the area, and take a physical (active) impression using a silicone-based agent, thereby subjecting the patient to some discomfort during the process. The next step requires the dentist to place a temporary crown over the area and then schedule the patient for an additional visit once the final crown based on the original impression has been manufactured by a laboratory. During this time, the patient is more subject to local infections. The entire process of mold-taking and re-shaping of materials at the laboratory is involved, is rather cumbersome and outdated, and it contains several steps that must be controlled by tight tolerances.

Intraoral, in-vivo passive 3D scanning is a rather challenging task. A multitude of technical and economic factors impose numerous constraints and add difficulties to the problem. For these reasons, successful systems must address and solve all these challenges, rendering them much more complex than otherwise conceptually simple 3D scanners. First, consider the operating environment, i.e. intraoral on a live patient. Digital imaging complications arise due to the restricted operating volume imposing a certain arrangement of optics and sensors such as to facilitate practical system operation in-vivo and intraoral as a probing device. Further, this environment is dark, contains air with a high degree of relative humidity expunged from the patient's lungs with every breath, and it facilitates artifact contamination of areas of interest by the mere presence of saliva, air bubbles within it and the patient's tongue itself. In addition, the environment is not static, as the patient is not a still unanimated object.

Second, consider the operator, i.e. the dentist. The device must be ergonomically designed around the system to ensure it is a useful tool and can solve the problem. Power consumption and power dissipation are important considerations. Moreover, as a hand-held medical device, it must pass additional regulatory affairs imposed by government authorities, as well as comply with the local standard electromagnetic interference/emission laws.

Third, consider the quality of the data obtained in the scanning process; if not comparable or better with current active (i.e. mold) impression-taking, the whole process is rendered null. The quality and accuracy of the data must also be consistent with the requirements of the CAM step of the process. Ultimately how well a milled restoration fits a patient's preparation area is a function of all of these factors.

There are several commercially-available solutions, including systems that integrate the CAM component. Some solutions still rely on contrast enhancing agents applied as a spray on the preparation area to mitigate some of the difficulties of imaging intra orally in-vivo. The 3D scanning implementations available employ several methods for obtaining surface topography estimations. These range from solutions exploiting depth map generation by confocal imaging, to fringe projection assisted 3D imaging, although other approaches such as correspondence-assisted stereoscopic imaging or plenoptic imaging may be used. Typically, the highest degree of data accuracy and ease of use, coupled with the economics and availability of off the shelf components, is greatly facilitated by employing a structured light projection technique, such as provided by a commercial system such as E4D Dentist, from E4D Technologies, LLC, of Dallas, Tex.

BRIEF SUMMARY

An intra-oral scanning device includes a light source and an optical system, and communicates with a display system. The device captures images of an object of interest, e.g., patient teeth or associated anatomy, by projecting the light source as a first series of frames, and a second series of frames. The first series of frames projects first pattern data, and the second series of frames projects second data. According to this disclosure, the second series of frames are interleaved between frames in the first series of frames. The frames in the first series are partially-illuminated (in that they include a pattern) and are used to capture data for a 3D model. The frames in the second series are preferably fully-illuminated (in that they do not include any pattern) and are used to generate a live preview of the object. By displaying the live preview frames in juxtaposition to the 3D model, the operator is provided with visual feedback of the object. The full illumination frames are used for texturing the 3D model generated by the partially-illuminated frame data. In one sequence, a first set (e.g., six) pattern frames are used, interspersed with a second set (e.g., three) illumination frames, for a sequence total of nine total CCD frames.

The foregoing has outlined some of the more pertinent features of the subject matter. These features should be construed to be merely illustrative.

BRIEF DESCRIPTION OF THE DRAWINGS

For a more complete understanding of the disclosed subject matter and the advantages thereof, reference is now made to the following descriptions taken in conjunction with the accompanying drawings, in which.

DETAILED DESCRIPTION

Figure 1:
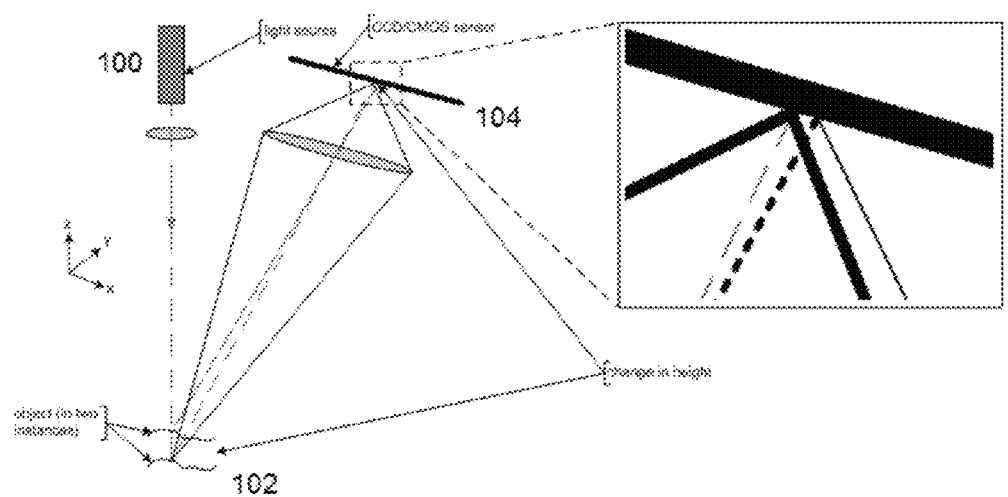
FIG. 1 illustrates basic components and geometry underlying 3D triangulation.

The principles behind structured light based 3D triangulation are explained in various works. The underlying principles are described with respect to FIG. 1, which illustrates a light source 100 directed to an object 102, with the reflection being captured a charge coupled device (CCD) imaging surface 104. This illustrates the basic components and principles behind 3D triangulation in an intuitive manner. In this approach, a change in height due to object topography is registered as a deviation of a projected point onto a charge coupled device (CCD) imaging surface. In operation, a laser pattern is projected with the help of an LCOS (i.e. liquid crystal on silicon) device. In particular, a sequence of a set of lines is generated by the lines reflected from LCOS to form a set of planes, or, if distortion is involved (as typically is the case when implemented), a set of conical or ruled surfaces.

Figure 2:
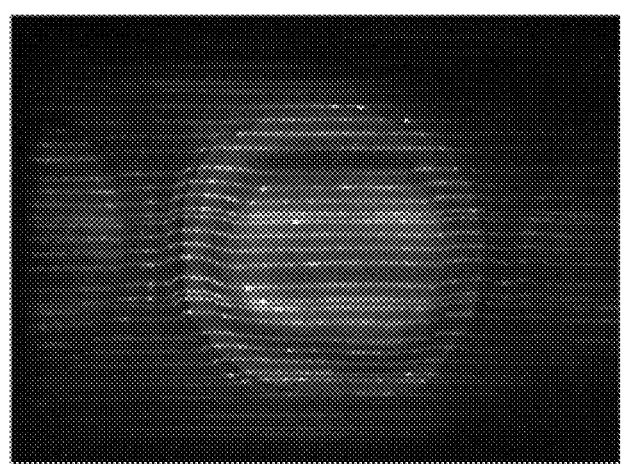
FIG. 2 is a known technique to project laser pattern lines onto a preparation area using an intra-oral hand-held wand device.
Figure 3:
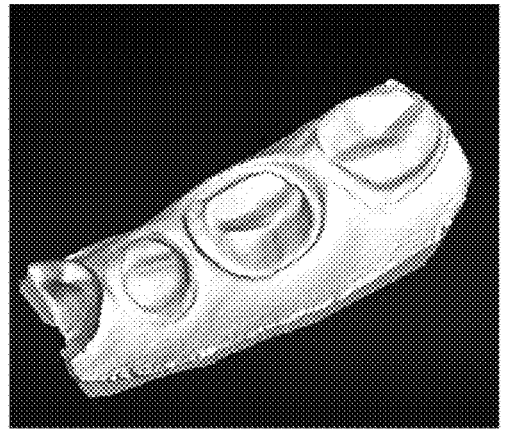
FIG. 3 illustrates a 3D generated model created by processing the partially-illuminated pattern lines.

FIG. 2 illustrates a pattern projected onto a preparation area. In an analogous manner, each point in the camera CCD frame corresponds to a line in space that passes through the imaging center or focal point. Because preferably the LCOS and the camera are laterally separated, the point of intersection between each laser surface generated by a single LCOS pixel and each line of sight is well-defined. Thus, by knowing the pixel coordinates on the camera matrix and the shape of the laser surface, it is possible to obtain coordinates of a 3D point corresponding to that pixel. When laser lines are projected onto the surface of the scanned object, the image of those lines in the camera plane defines a set of 3D points corresponding to the object surface. To obtain the shape of the surfaces formed to each laser line, a calibration procedure is performed. A camera lens calibration is performed by taking an image of a checkerboard pattern, with a set of intrinsic camera parameters (such as focal length and lens distortion) estimated as a result. From this, an exact direction of a ray corresponding to each camera pixel is established. To determine the shape of the laser surfaces, a set of planes located at the known distances with known orientation are scanned. Each line projected onto each successive plane forms an image on the CCD matrix, represented as a set of pixels and, because for each pixel the corresponding direction and the actual distance to the calibration plane are known, the set of 3D coordinates forming a line of intersection between a laser surface and calibration plane are known as well. Interpolation between successive lines produces the shape of the laser surface, represented by the final generated 3D model shown in FIG. 3.

The frames used to capture the data for the 3D model are partially-illuminated frames (such as shown in FIG. 2, wherein the LCOS paints a series of lines in a pattern). According to this disclosure, and to facilitate the operation of the device and provide live video as feedback to the operator (as well as the 3D-computed data), a preferred implementation uses a sequence of patterns throughout which full illumination frames are selectively interspersed. A full illumination frame involves all or substantially all lines being turned on, as compared to the partially-illuminated approach shown in FIG. 2, wherein only some lines are projected. In a full illumination frame, in effect there is no pattern. The partially-illustrated frames provide the data from which the 3D coordinates of the surface are determined. A technique for rendering frames in this manner is described in U.S. Pat. No. 7,184,150, the disclosure of which is incorporated herein by reference. In contrast, the full illumination frames are used for texturing the 3D model generated by the partially-illuminated frame data. In one sequence, a first set (e.g., six) pattern frames are used, interspersed with a second set (e.g., three) illumination frames, for a sequence total of nine total CCD frames. A software traffic shaper is then used to separate captured frames in two streams, namely, a live preview stream, and a data processing stream from which the 3D model is generated. If necessary, e.g., for computational or storage efficiencies, the live preview stream can give up priority and drop some frames when the CPU work load exceeds a certain limit.

In the embodiment described above, the same light source (e.g., a blue laser) is used to generate both the first series of frames and the second series of (interleaved) frames, and a monochrome sensor is used. If it is desired to output a color video preview, one or more other light sources (e.g., a red laser, a green laser, or some combination) are used to vary the color of the full illumination frames. Thus, in one alternative embodiment, there are three different light sources (blue, red and green), with the resulting data returned from these full illumination frames then being used to provide a color video preview. As yet another alternative, full illumination frames are generated using a source of monochrome light, and a color sensor is used to receive the reflected data (to generate the color video preview). Still another alternative to generate a color video image is to use full illumination red and green frames with a partial illumination blue frame. Other light sources (e.g., a red/green laser or even an LED) may obviate the full illumination blue frame. Another possibility is to use red as the additional color (leaving out the green, or vice versa), and then processing the resulting data to generate a pseudo-color video stream. When the approach uses the red, green and blue laser, the scanner may be used to generate a simplified optical coherence tomography (OCT) scan using discrete lasers instead of a single broadband source, or a swept source.

Figure 4:
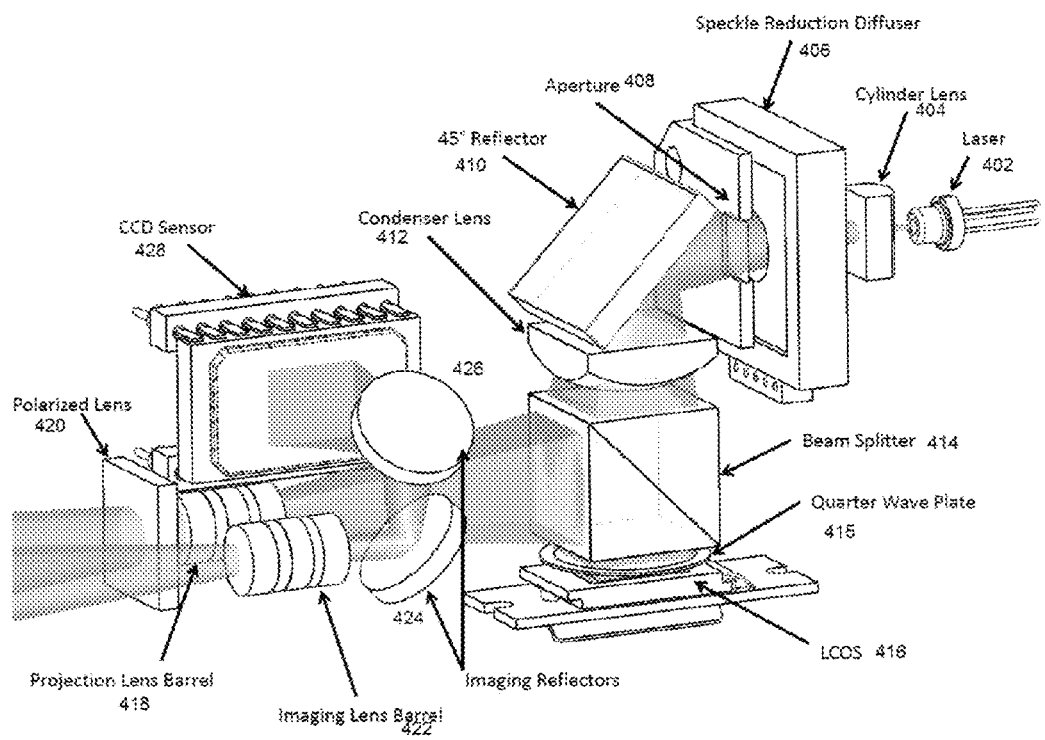
FIG. 4 illustrates an optical sub-system of an intra-oral scanning device of this disclosure with its outer housing removed.

FIG. 4 illustrates an embodiment of an optical sub-system of an intra-oral device with its outer housing removed. The primary imaging components of the optical sub-system 400 include a laser 402, a cylinder lens 404, a speckle reduction diffuser 406, an aperture 408, a reflector 410, a condenser lens 412, a beam splitter 414, a quarter wave plate 415, the LCOS device assembly 416, a projection lens barrel assembly 418, and a polarized lens 420. A return (imaging) path comprises imaging lens barrel assembly 422, first and second imaging reflectors 424 and 426, and the CCD sensor 428.

Without meant to be limiting, a preferred laser is a blue laser device with a wavelength of 450 nm, and thus the optical path for the projection side is polarization-based. In this embodiment, projection is achieved with the LCOS device 416 having a resolution of 800 by 600 pixels and a pixel size of 8.0 um. The speckle reduction diffuser (a de-speckle component) is used to eliminate the speckle issues otherwise caused by using a laser as the light source. Using a laser (instead of, for example, an LED light source) produces a much brighter projected pattern which, in turn, allows the scanner to image intra-orally without powder.

Figure 5:
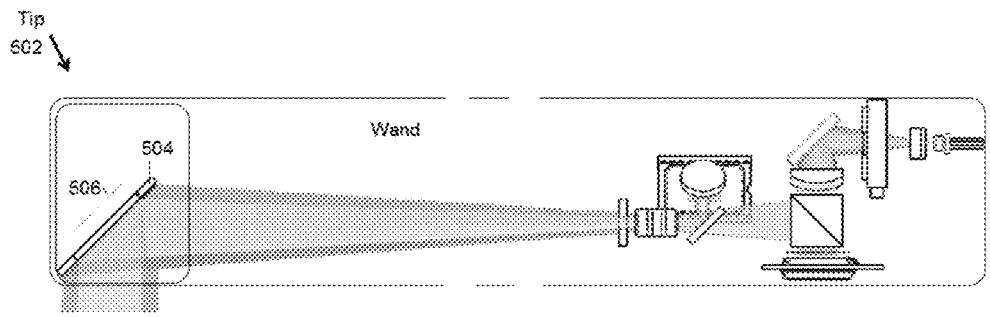
FIG. 5 is an elevation view of the intra-oral scanning device of this disclosure illustrating a removable tip that includes a heating element.
Figure 9:
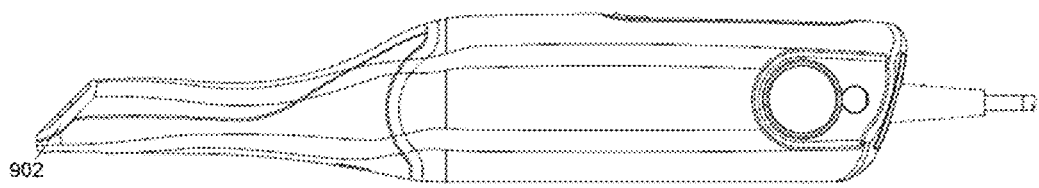
FIG. 9 is an elevation view of the scanning device.

As seen in FIG. 5, the intra-oral device 500 is configured as a hand-held wand that includes a tip portion or "tip" 502. FIG. 9 illustrates an embodiment of the wand with the outer housing present. As seen in FIG. 5, the tip 502 includes a mirror 504 and preferably no additional glass windows; the mirror 504 reflects the projection path from a long axis of the device (the optical sub-system shown in FIG. 4) towards the target area being scanned, and that receives the imaging path data returned from the target area. The returned data is forwarded down the long axis of the device, where it is imaged by the CCD sensor device. By using a mirror 504 in the tip 502, the possibility of a surface near the target area being contaminated with dirt or fluid is reduced. This is desirable, as any contamination on a glass window or prism surface may be close to (or within) a focused region of the optical path, and therefore may result in erroneous measurements. The reflecting mirror 504 is outside the focus region, and thus any slight imperfections or debris on its surface will not result in erroneous data measurements. Preferably, the tip 502 is removable from the rest of the wand housing, and the mirror is heated (with an active heating element 506) to prevent fogging of the optical surfaces while the device is being deployed intra-orally. The heating element may be a metal conductive element that is supported in a molded plastic housing and that receives current from other wand electronics. Any other type of heating element may be used. FIG. 9 illustrates the removable tip 902. In this manner, multiple tips (the others now shown), each with varying mirror angles and sizes, may be implemented with a single wand body that includes the optical sub-system shown in FIG. 4. In this manner, different tips may be used for different scanning scenarios, such as scanning posterior preparations in small patients, or more challenging situations where a steeper viewing angle is required.

Figure 6:
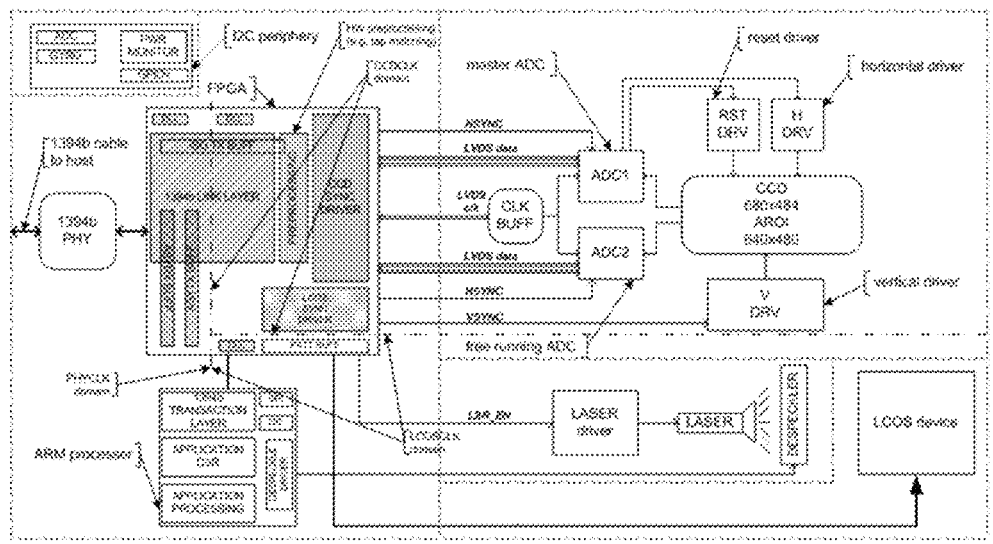
FIG. 6 is an embodiment of system architecture to control the hand-held intra-oral device of this disclosure.

FIG. 6 illustrates system architecture for the wand. In this implementation there are three (3) subsystems, namely, an imaging sub-system, a projection/illumination sub-system, and a periphery sub-system. Preferably, imaging is achieved by an over-clocked dual-tap CCD with an active resolution of 648 by 484 pixels, and a pixel size of 9 um.

In this embodiment, which is not intended to be limiting, the system architecture comprises a tightly-integrated IP FPGA core containing an IEEE 1394b S800 link layer, CCD/ADC synchronizers, the LOCS and illumination synchronizer. Cross-clock domain FIFOs are implemented to synchronize the CCD exposure/LCOS projection/CCD readout sequence to the IEEE1394 bus clock, which is 125 us or 8000 Hz. The FPGA is assisted by an ARM processor, implementing the IEEE1394b transaction layer and various housekeeping system tasks, such as running an I2C periphery priority task scheduler. The FPGA implements deep FIFOs for asynchronous packet reception and transmission and likewise for the CCD video data, which is sent as isochronous packets. It also implements a prioritized interrupt mechanism that enables the ARM processor to de-queue and en-queue IEEE1394 asynchronous packets and to complete them according to the bus transaction layer specification and various application requirements. The bulk of the housekeeping work in the system originates in user space software, ends up as an asynchronous packet in the ARM processor and is dispatched from there through either I2C or SPI to the appropriate peripheral component. The software is designed to maintain the hardware pipelining while running within a non-real time operating system (OS), such as Microsoft® Windows 7 and Apple® OS/X. Other operating systems such as Android or iOS® may be used.

Figure 7:
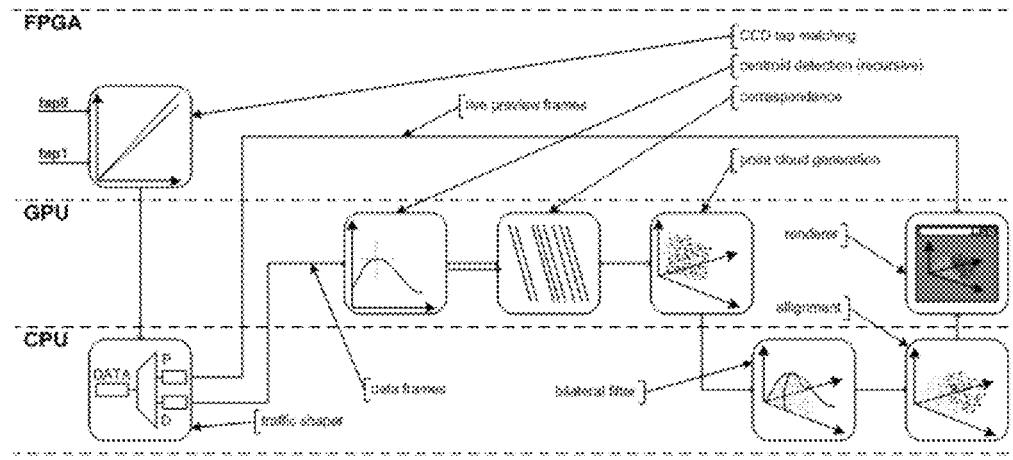
FIG. 7 illustrates a preferred 3D pipeline processing approach implemented in the device.

In this embodiment, and to provide the required data quality at a desired rate, the imaging system preferably is comprised of a slightly over-clocked dual tapped CCD. The CCD is 680 by 484 pixels containing some dark columns and rows for black offset correction and is specified to have 57 dB of dynamic range at a pixel clock of 20 MHz with a maximum pixel clock of 30 MHz. The projection and illumination subsystem comprises LCOS device, a laser diode driver, a 450 nm blue laser diode and an optical de-speckling device. As illustrated in FIG. 7, preferably data is processed in a pipeline distributed across several computing resources. In this approach, data from the CCD ADCs, 8 bit per pixel, is first run through a tap matching block where both taps are linearized and matched according to a look up table. This implies a previous calibration step. The traffic shaper separates the data into live preview and 3D processing input frames. The 3D processing input frames contain projected patterns. On the GPU these frames are first run through a centroid detector implemented as a recursive sub-pixel edge detector, a correspondence block, and finally a point cloud generation block. This output is then run on the CPU side through a bilateral filter for data smoothing, and through an alignment block to stitch scans together. This processing distribution allows for running alignment in a pipelined fashion with 3D point cloud generation happening in parallel.

Preferably, fast imaging is used to allow minimization of errors (e.g., due to operator hand jitter). In one embodiment, good results were obtained with a live preview window of approximately 20 frames per second, coupled with approximately 15 frames per second for the 3D data.

Figure 8:
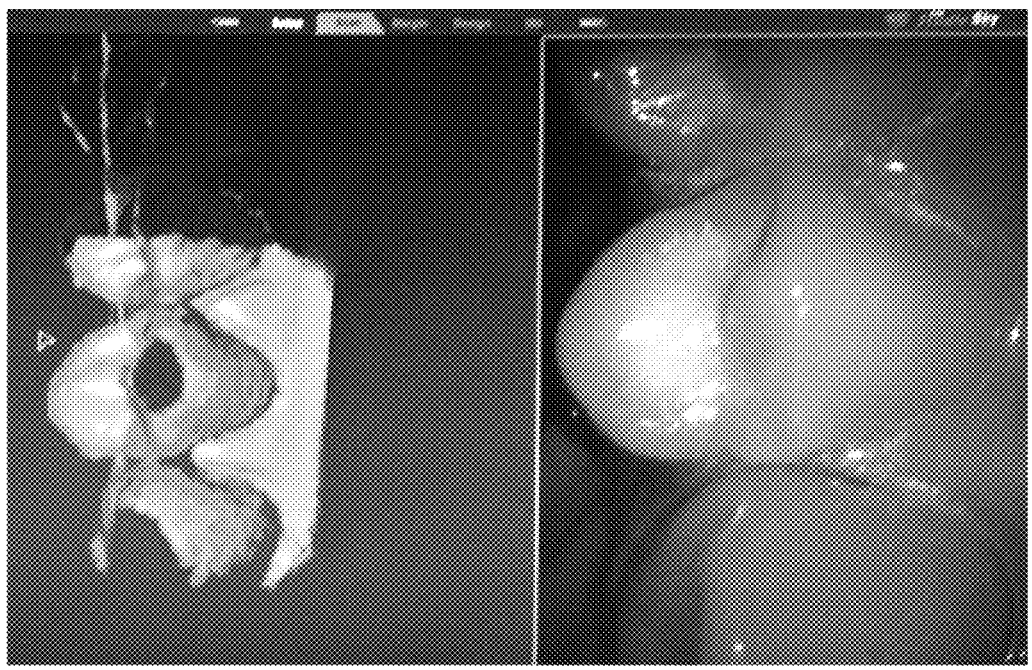
FIG. 8 illustrates the rendering of a textured 3D model juxtaposed against a live video feed provided by the scanning techniques of this disclosure.

A representative display interface is used to display the 3D model, on the one hand, and the live video preview window, on the other. FIG. 8 illustrates a representative screen grab from a juxtaposition of these views. These views may be juxtaposed in any convenient display format (e.g., side-by-side, above-below, as an overlay (or "3D texture" view), or the like).

More generally, the display method is implemented using one or more computing-related entities (systems, machines, processes, programs, libraries, functions, code, or the like) that facilitate or provide the above-described functionality. Thus, the wand (and its system architecture) typically interface to a machine (e.g., a device or tablet) running commodity hardware, an operating system, an application runtime environment, and a set of applications or processes (e.g., linkable libraries, native code, or the like, depending on platform), that provide the functionality of a given system or subsystem. The interface may be wired, or wireless, or some combination thereof, and the display machine/device may be co-located (with the wand), or remote therefrom. The manner by which the display frames are received from the wand is not a limitation of this disclosure.

In a representative embodiment, a computing entity in which the subject matter implemented comprises hardware, suitable storage and memory for storing an operating system, one or more software applications and data, conventional input and output devices (a display, a keyboard, a gesture-based display, a point-and-click device, and the like), other devices to provide network connectivity, and the like.

Generalizing, the intra-oral digitizer wand of this disclosure is associated with the workstation to obtain optical scans from a patient's anatomy. The digitizer scans the restoration site with a scanning laser system and delivers live images to a monitor on the workstation. The techniques of this disclosure thus may be incorporated into an intra-oral digital (IOD)

scanner and associated computer-aided design system, such as E4D Dentist™ system, manufactured by D4D Technologies, LLC. The E4D Dentist system is a comprehensive chair-side CAD CAM system that produces inlays, onlays, full crowns and veneers. A handheld laser scanner in the system captures a true 3-D image either intra-orally, from impressions or from models. Design software in this system is used to create a 3-D virtual model.

Generalizing, a display interface according to this disclosure is generated in software (e.g., a set of computer program instructions) executable in at least one processor. A representative implementation is computer program product comprising a tangible non-transitory medium on which given computer code is written, stored or otherwise embedded. The display interface comprises an ordered set of display tabs and associated display panels or "viewports." Although the illustrative embodiment shows data sets displayed within multiple viewports on a single display, this is not a limitation, as the various views may be displayed using multiple windows, views, viewports, and the like. The display interface may be web-based, in which case the views of displayed as markup-language pages. The interface exposes conventional display objects such as tabbed views, pull-down menus, browse objects, and the like.

Although not meant to be limiting, the technique described above may be implemented within a chair-side dental item CAD/CAM system.

While the above describes a particular order of operations performed by certain embodiments of the described subject matter, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature, structure, or characteristic. Further, while given components of the system have been described separately, one of ordinary skill will appreciate that some of the functions may be combined or shared in given systems, machines, devices, processes, instructions, program sequences, code portions, and the like.

Having described our invention, what we now claim is as follows.

The invention claimed is:

1. A scanning and display method, comprising:
projecting, using a light source, first pattern data, and second data, the first pattern data projected within a first series of frames, the second data projected within a second series of frames, the second series of frames interleaved between frames in the first series of frames as a single composite set of frames;
receiving first reflection data reflected from an object from the first pattern data;
receiving second reflection data reflected from the object from the second data;
processing, using a computing entity comprising software executing in hardware, the first reflection data to generate first information representing a 3D model of the object;
processing, using the computing entity, the second reflection data to generate second information representing a live video preview of the object; and
rendering, as a single composite set of display frames, the 3D model of the object juxtaposed against the live video preview.

2. The method as described in claim 1 wherein the first series of frames includes one or more frames that are each partially-illuminated, and the second series of frames includes one or more frames that are fully-illuminated.

3. The method as described in claim 1 wherein the projecting step is carried out using an liquid crystal on silicon (LCOS) device.

4. The method as described in claim 3 wherein the light source is a blue laser.

5. Apparatus, comprising:
one or more light sources;
a processor;
computer memory holding computer program instructions executed by the processor to:
control the one or more light sources to project first pattern data, and second data, the first pattern data projected within a first series of frames, the second data projected within a second series of frames, the second series of frames interleaved between frames in the first series of frames as a single composite set of frames;
to receive first reflection data reflected from an object from the first pattern data;
to receive second reflection data reflected from the object from the second data;
to process the first reflection data to generate first information representing a 3D model of the object;
to process the second reflection data to generate second information representing a live video preview of the object; and
to enable rendering, as a single composite set of display frames, of the 3D model of the object juxtaposed against the live video preview.

6. The apparatus as described in claim 5 wherein the one or more light sources comprise a single color laser.

7. The apparatus as described in claim 5 further including a mirror to project the first and second pattern data, and to receive the first and second reflection data.

8. The apparatus as described in claim 7 further including a heating element to heat the mirror.

9. The apparatus as described in claim 7 further including a housing, the housing including an interchangeable tip, the mirror supported in the interchangeable tip.

10. The apparatus as described in claim 5 wherein the first series of frames includes one or more frames that are each partially-illuminated, and the second series of frames includes one or more frames that are fully-illuminated.

11. The apparatus as described in claim 5 wherein the one or more light sources comprise a first light source to project the first series of frames, and second light source to project the second series of frames.

12. The apparatus as described in claim 11 wherein the first light source and the second light source project different colors.

13. An article associated a light source and comprising a non-transitory machine readable medium that stores a program, the program being executed by a machine:
to control the one or more light sources to project first pattern data, and second data, the first pattern data projected within a first series of frames, the second data projected within a second series of frames, the second series of frames interleaved between frames in the first series of frames as a single composite set of frames;
to receive first reflection data reflected from an object from the first pattern data;
to receive second reflection data reflected from the object from the second data;

to process the first reflection data to generate first information representing a 3D model of the object;

to process the second reflection data to generate second information representing a live video preview of the object; and to render, as a single composite set of display frames, the 3D model of the object juxtaposed against the live video preview.

14. The article as described in claim 11 wherein the first series of frames includes one or more frames that are each partially-illuminated, and the second series of frames includes one or more frames that are fully-illuminated.

* * * * *